(12) United States Patent
Keach (10) Patent No.: US 12,121,280 B2
(45) Date of Patent: Oct. 22, 2024

(54) INTRAMEDULLARY NAIL EXTRACTOR

(71) Applicant: Shukla Medical, St. Petersburg, FL (US)

(72) Inventor: Nicholas Christopher Keach, Lutz, FL (US)

(73) Assignee: Shukla Medical, St. Petersburg, FL (US)

( * ) Notice: Subject to any disclaimer, the term of this patent is extended or adjusted under 35 U.S.C. 154(b) by 213 days.

(21) Appl. No.: 17/302,246

(22) Filed: Apr. 28, 2021

(65) Prior Publication Data

US 2021/0338301 A1 Nov. 4, 2021

Related U.S. Application Data (60) Provisional application No. 63/018,568, filed on May 1, 2020.

(51) Int. Cl.
| | |
|---|---|
| *A61B 17/92* | (2006.01) |
| *G09F 3/00* | (2006.01) |
| *A61B 17/00* | (2006.01) |
| *G09F 3/02* | (2006.01) |

(52) U.S. Cl.
CPC .......... *A61B 17/921* (2013.01); *G09F 3/0291* (2013.01); *A61B 2017/00477* (2013.01); *G09F 2003/0226* (2013.01); *G09F 2003/0242* (2013.01)

(58) Field of Classification Search
CPC ..... A61B 17/921; A61B 17/92; A61B 17/808; A61F 2/4603; A61F 2/4607; A61F 2002/4619; A61F 2002/4622; A61F 2002/4625; A61F 2002/4627; B25B 9/00; B25B 5/00; B25B 5/067; B25B 5/082; B25B 5/10; B25B 5/101; B25B 5/109
USPC ................................ 269/3, 6, 248, 143, 249
See application file for complete search history.

(56) References Cited

U.S. PATENT DOCUMENTS

| | | | |
|---|---|---|---|
| 2,528,941 A | 11/1950 | Bassett et al. | |
| 4,399,813 A | 8/1983 | Barber | |
| 4,531,517 A | 7/1985 | Forte et al. | |
| 5,013,314 A | 5/1991 | Firica et al. | |
| 6,991,656 B2 * | 1/2006 | Mears | B25B 7/02 623/22.4 |
| 7,476,225 B2 * | 1/2009 | Cole | A61B 17/16 606/62 |
| 8,777,960 B2 * | 7/2014 | Murray | A61B 17/8888 606/104 |
| 10,238,439 B2 * | 3/2019 | Prybis | A61B 17/80 |

(Continued)

OTHER PUBLICATIONS

Extended European Search Report mailed Oct. 15, 2021 in EP Application No. 21171508.1.

*Primary Examiner* — Tracy L Kamikawa
(74) *Attorney, Agent, or Firm* — Kim IP Law Group LLC (57) ABSTRACT

An intramedullary nail extractor including a central body, a rotatable sleeve and a clamping member. The central body includes a proximal end for attachment to an extractor, a distal end having a hook for engaging an intramedullary nail, and a threaded intermediate portion between the proximal end and the distal end. The rotatable sleeve threadedly engages the threaded intermediate portion of the central body, and the clamping member is operatively engaged by the rotatable sleeve and moveable relative to the central body.

11 Claims, 11 Drawing Sheets

(56) References Cited

U.S. PATENT DOCUMENTS

| | | | |
|---|---|---|---|
| 2008/0077241 A1* | 3/2008 | Nguyen | A61F 2/4684 606/85 |
| 2009/0326543 A1* | 12/2009 | Fabian, Jr. | A61F 2/4611 128/898 |
| 2012/0290099 A1* | 11/2012 | Gibson | A61F 2/4637 623/20.11 |
| 2016/0270836 A1 | 9/2016 | Ferreira et al. | |

\* cited by examiner

INTRAMEDULLARY NAIL EXTRACTOR

CROSS-REFERENCE TO RELATED APPLICATION

This application claims the benefit under 35 U.S.C. § 119(e) to U.S. Provisional Application No. 63/018,569, filed May 1, 2020, entitled "Nail Hook Extractor with Screw Clamp," the entire disclosure of which is hereby incorporated by reference for all purposes.

BACKGROUND OF THE DISCLOSURE

The exemplary embodiments of present disclosure relate generally to a surgical extraction tool and, more specifically, to a tool for extracting an intramedullary nail from a bone, for example, a tibia, a femur or a humerus.

A typical intramedullary nail has an elongated generally cylindrical shape sufficient to be inserted in an intramedullary canal. Some intramedullary nails have an aperture adjacent a proximal end of the nail adapted to be engaged by an extractor tool. A disadvantage of conventional intramedullary extractor tools is that they tend to slip out of or disengage from the aperture in the nail thereby rendering extraction of the nail difficult, especially if the nail is firmly embedded in bone.

BRIEF SUMMARY OF THE DISCLOSURE

In accordance with an exemplary embodiment there is provided an intramedullary nail extractor that includes a central body, a rotatable sleeve and a clamping member. The central body includes a proximal end for attachment to an extractor, a distal end having a hook for engaging an intramedullary nail, and a threaded intermediate portion between the proximal end and the distal end. The rotatable sleeve threadedly engages the threaded intermediate portion of the central body, and the clamping member is operatively engaged by the rotatable sleeve and moveable relative to the central body.

According to an aspect, the hook includes an arm having a longitudinal axis that is radially offset from a longitudinal axis of the central body.

According to an aspect, the clamping member is a clamping rod. According to another aspect, the clamping member includes a distally facing distal end for contacting the intramedullary nail. According to another aspect, the clamping member includes a plurality of through holes. According to another aspect, the clamping member includes a distally facing aperture for passage of the distal end of the central body therethrough. According to another aspect, the hook extends through an aperture of the clamping member. According to another aspect, the clamping member includes a longitudinally extending slot for passage of the distal end of the central body therethrough. According to another aspect, the clamping member is retained within the rotatable sleeve by a raised annular ridge provided on the clamping member and configured for engaging an annular groove provided in the rotatable sleeve. According to another aspect, the clamping member includes a pin projecting distally from a distally facing distal end of the clamping member for engaging the intramedullary nail. According to another aspect, the clamping member includes a recess in a distally facing distal end of the clamping member for receiving the intramedullary nail. According to another aspect, the clamping member includes a high friction material affixed to a distally facing distal end of the clamping member for contacting the intramedullary nail.

In accordance with another exemplary embodiment there is provided a method of extracting an intramedullary nail from bone comprising the steps of inserting the aforementioned intramedullary nail extractor into bone, inserting the hook through an aperture of the intramedullary nail, rotating the rotatable sleeve to secure the clamping member against the intramedullary nail, and applying an extraction force to the proximal end of the central body.

Other features and advantages of the subject disclosure will be apparent from the following more detailed description of the exemplary embodiments.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the present disclosure, there are shown in the drawings exemplary embodiments. It should be understood, however, that the subject application is not limited to the precise arrangements and instrumentalities shown.

DETAILED DESCRIPTION OF THE DISCLOSURE

Reference will now be made in detail to the various exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject application in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art. "Exemplary" as used herein shall mean serving as an example.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Figure 1:
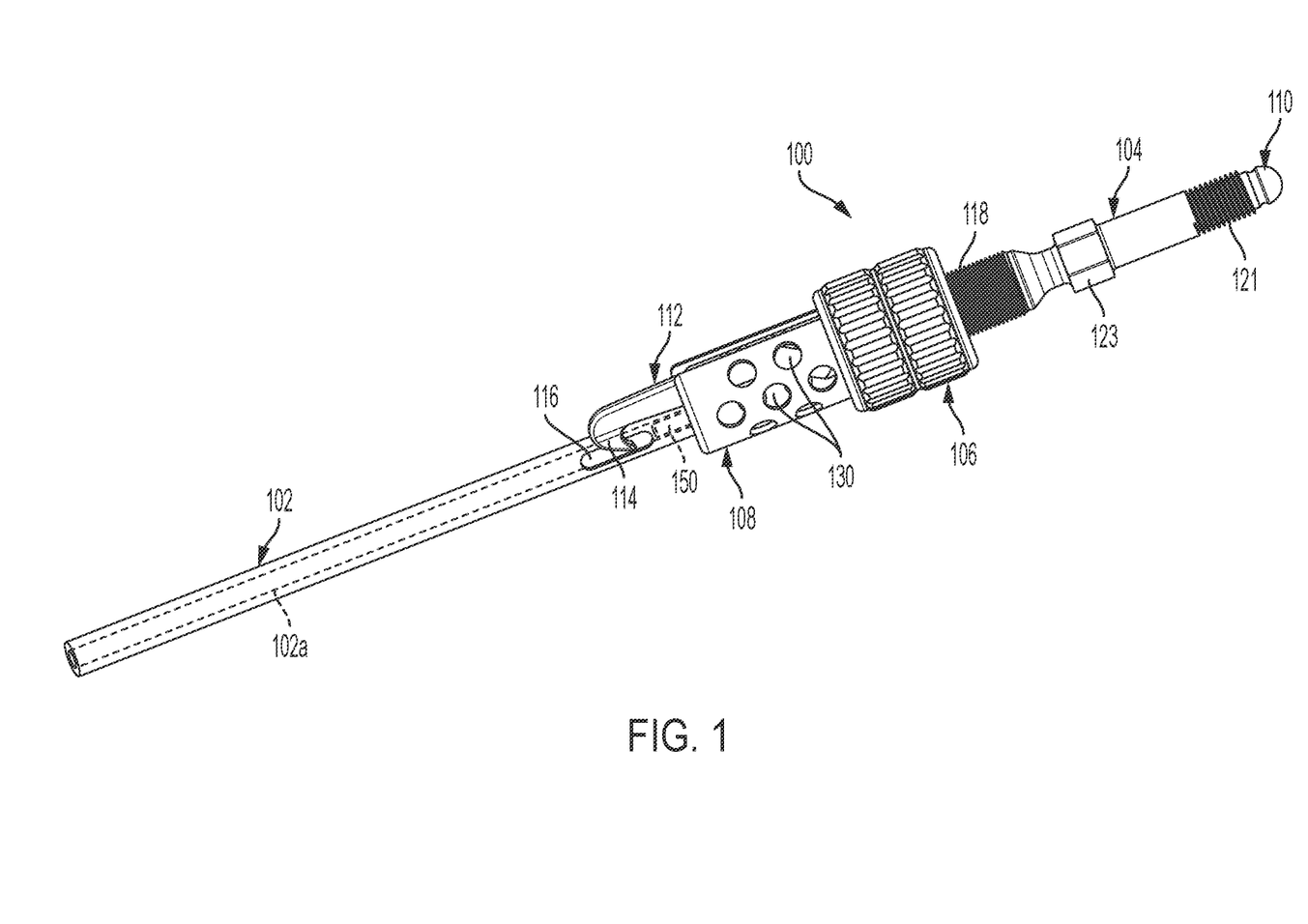
FIG. 1 is perspective view of an intramedullary nail extractor in accordance with an exemplary embodiment of the subject disclosure shown clamping an intramedullary nail.
Figure 2:
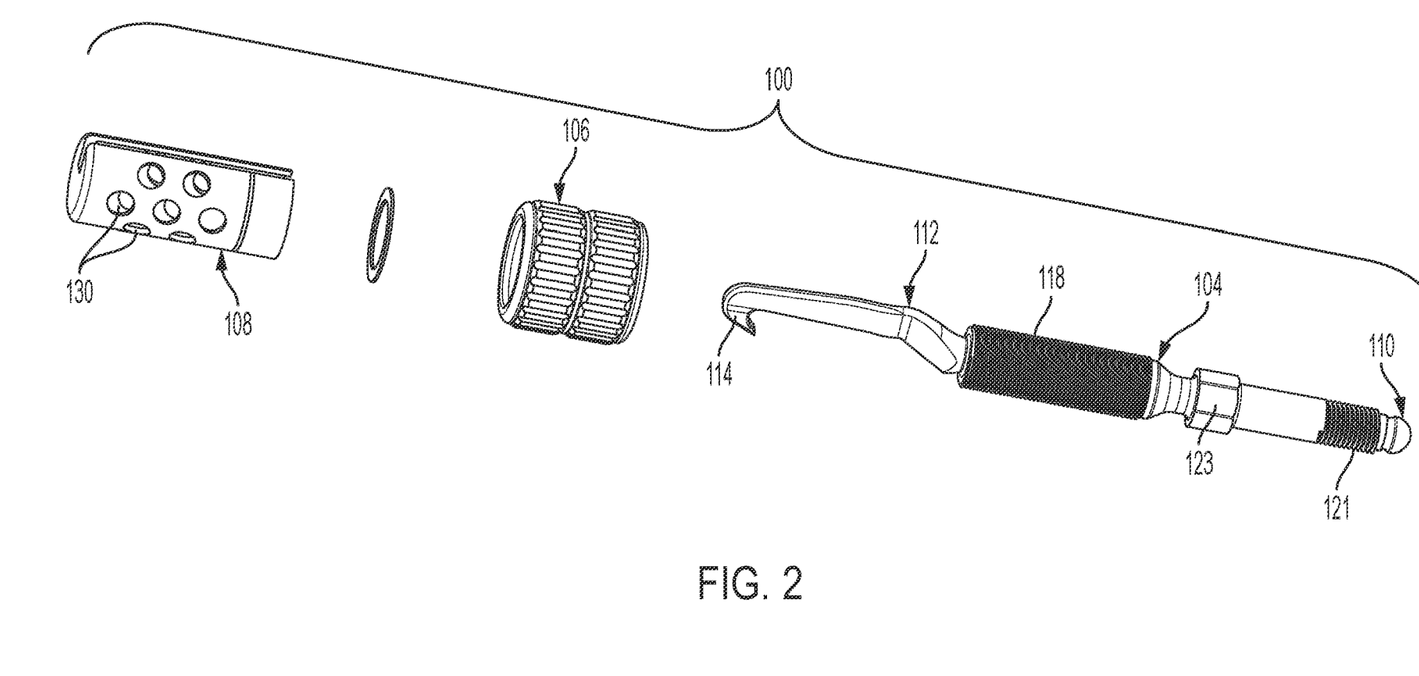
FIG. 2 is an exploded perspective view of the intramedullary nail extractor of FIG. 1.
Figure 8A:
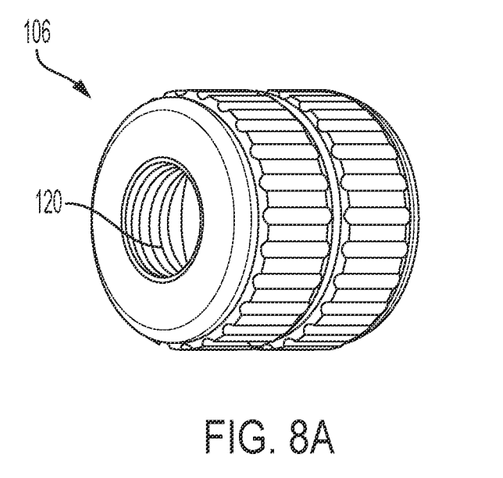
FIG. 8A is a proximal end perspective view of a rotatable sleeve of the intramedullary nail extractor of FIG. 1.
Figure 8B:
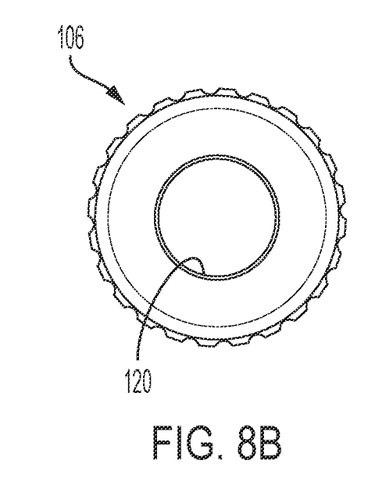
FIG. 8B is a proximal end view of the rotatable sleeve of FIG. 8A.
Figure 8C:
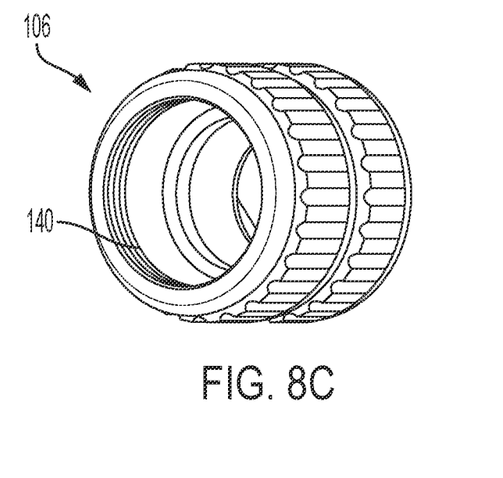
FIG. 8C is a distal end perspective view of a rotatable sleeve of FIG. 8A.
Figure 8D:
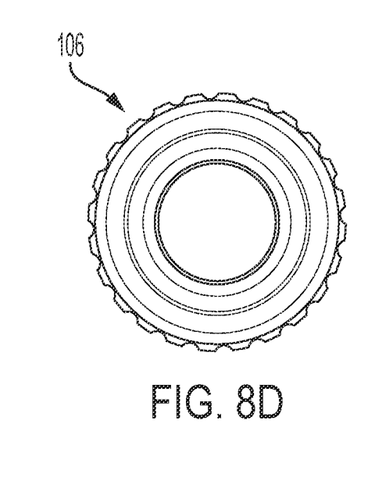
FIG. 8D is distal end view of the rotatable sleeve of FIG. 8A.
Figure 10:
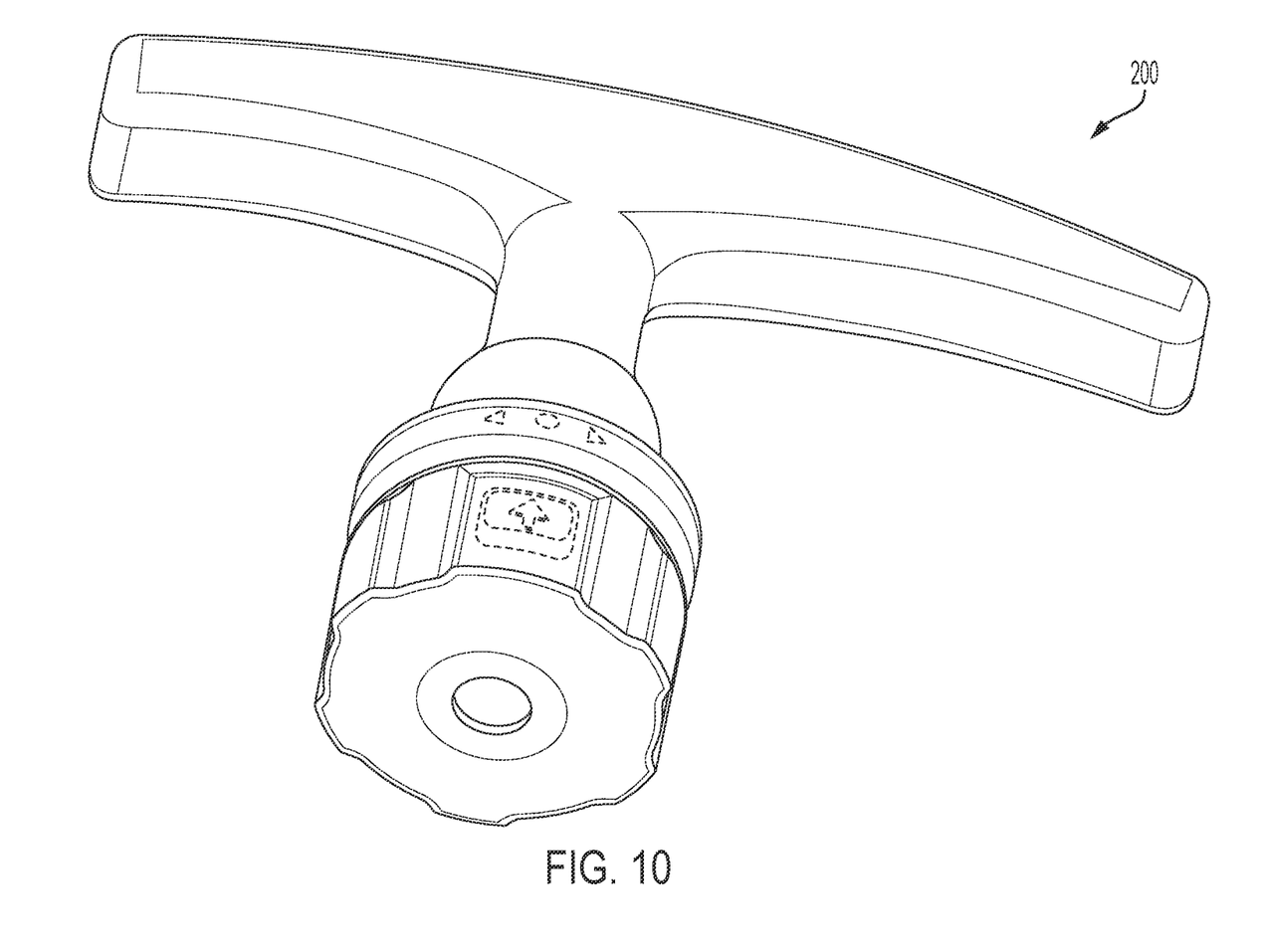
FIG. 10 is a perspective view of an extractor applicable for use with the intramedullary nail extractor of FIG. 1.

Referring now to the drawings, FIGS. 1-6 illustrate an intramedullary nail extractor 100 in accordance with an exemplary embodiment of the present disclosure. As shown in FIG. 1, the intramedullary nail extractor 100 is engaged with a cannulated intramedullary nail 102 having a longitudinal opening or passageway 102a which is embedded in an unillustrated bone such as, e.g., the tibia, the femur or the humerus. The intramedullary nail extractor 100 includes a central body 104, a rotatable sleeve 106 and a clamping member 108. The central body 104 includes a proximal end 110 for attachment to an extractor 200 (FIG. 10) such as, e.g., a T-handle, a C-handle, a slap hammer, a slide mallet, and the like. Extractors applicable to the intramedullary nail extractor are disclosed in U.S. Pat. Nos. D883,480, D912, 811 and D816,219, the disclosures of which are hereby incorporated by reference in their entirety for all purposes. The central body additionally includes a distal end 112 having a hook 114 for engaging an aperture 116 in the intramedullary nail 102 (FIG. 1), and a threaded intermediate portion 118 between the proximal end and the distal end. The rotatable sleeve 106 threadedly engages the threaded intermediate portion of the central body 104 at threading 120 (FIGS. 5 and 8A), and the clamping member 108 is operatively engaged by the rotatable sleeve and moveable relative to the central body.

The central body 104 is provided with structure for attaching the central body to an unillustrated extractor of the types noted above. According to an aspect, the extractor attachment structure is configured as threading 121. However, it may assume the form of any suitable attachment structure including, without limitation, a reduced diameter portion or a J-slot depending on the construction of the corresponding attachment structure of the extractor. Positioned between the threaded intermediate portion 118 and threading 121 is a raised multisided formation 123 which can be hexagonal, octagonal, or the like, that is adapted for engagement with a tool to stabilize in position the extractor or rotate the extractor relative to e.g., an extractor or intramedullary canal.

Figure 3:
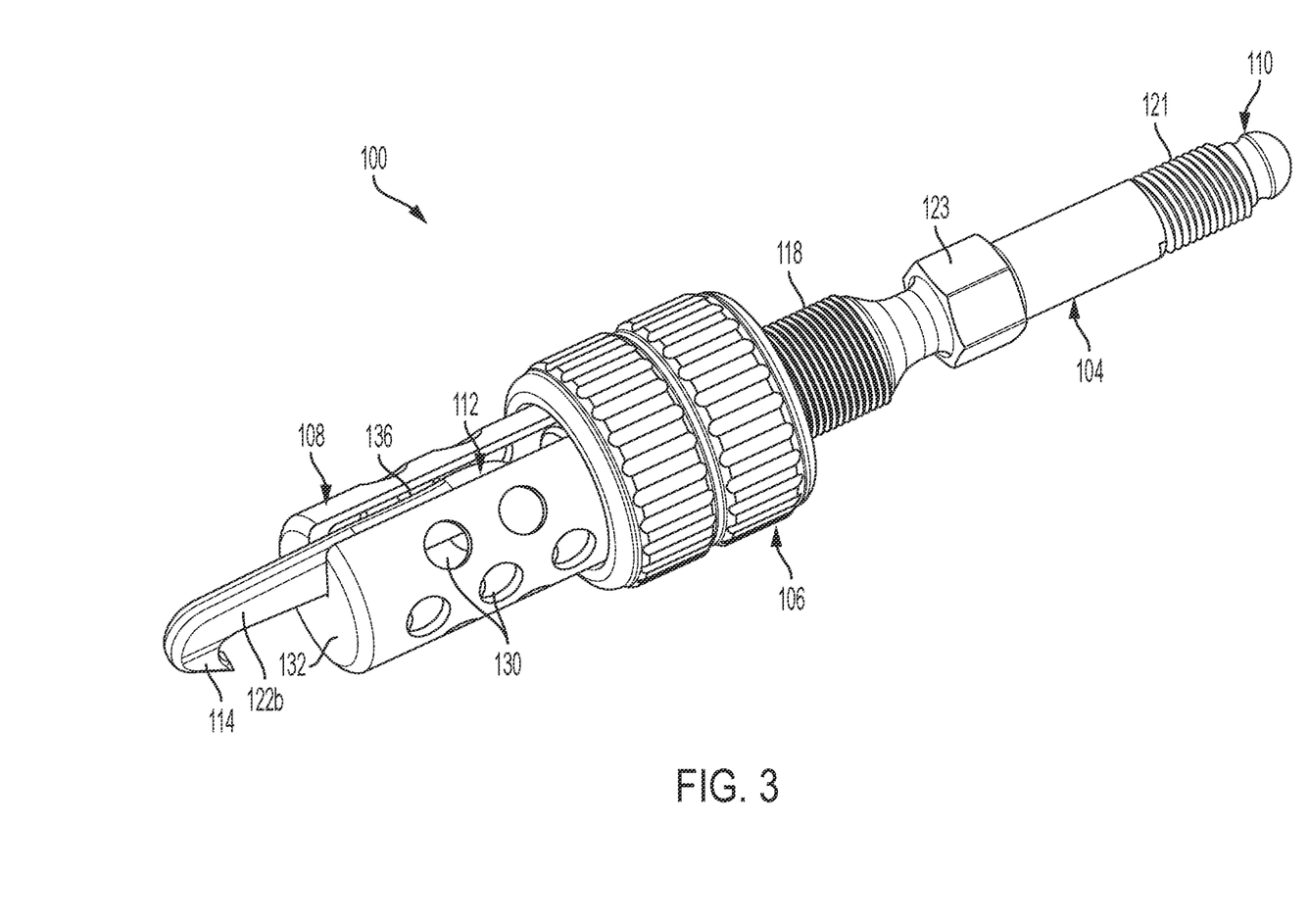
FIG. 3 is a perspective view of the intramedullary nail extractor of FIG. 1.
Figure 4:
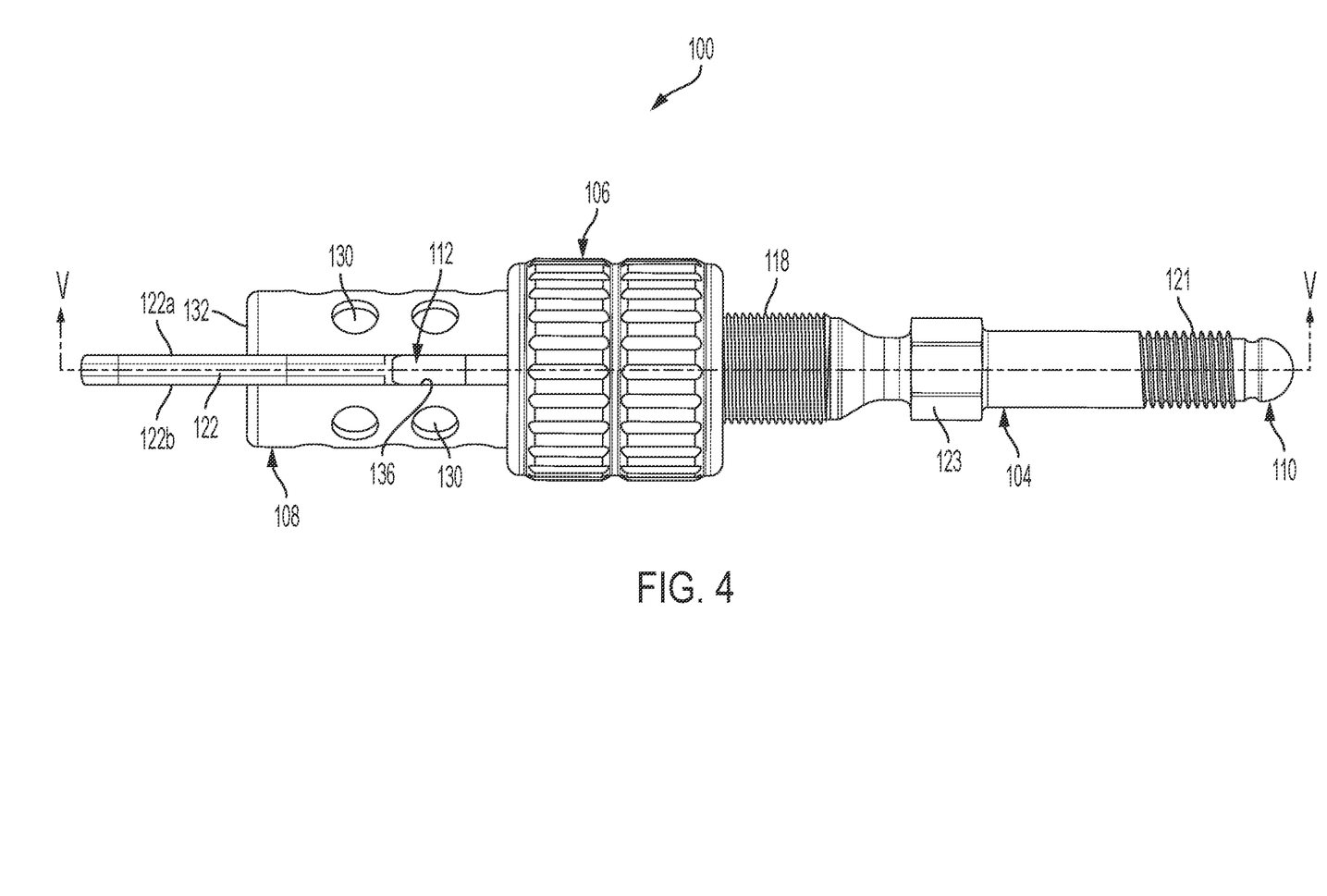
FIG. 4 is a side view of the intramedullary nail extractor of FIG. 1.
Figure 5:
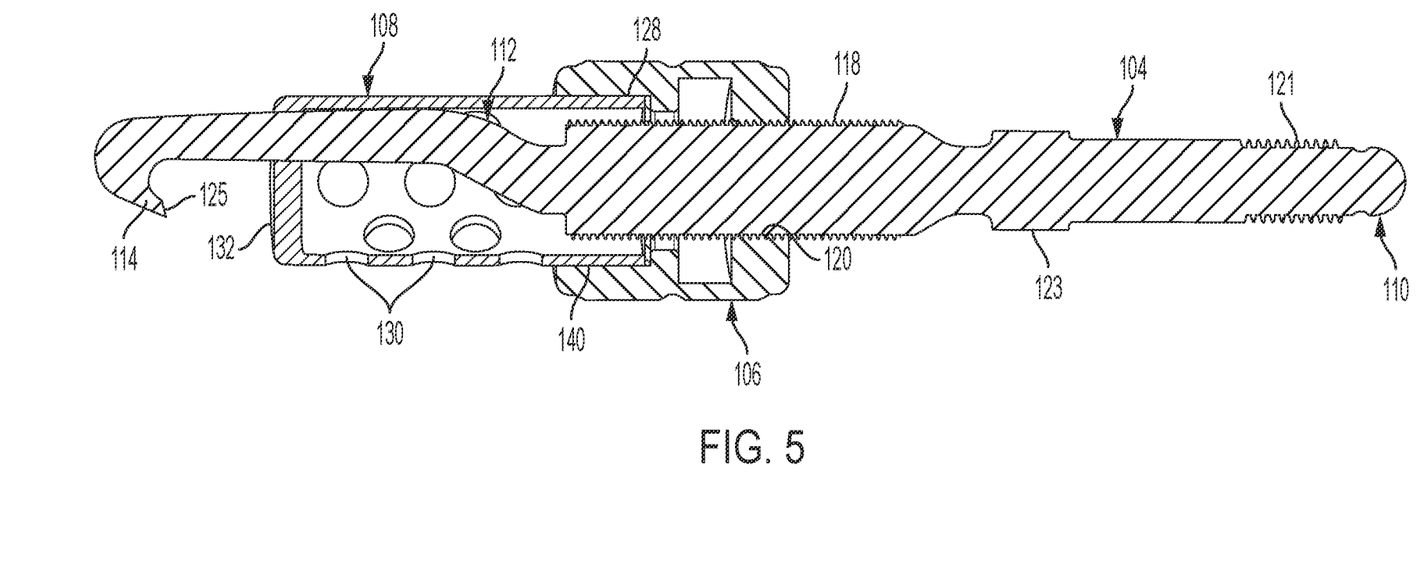
FIG. 5 is a cross-sectional view of the intramedullary nail extractor taken along line V-V of FIG. 4.
Figure 6:
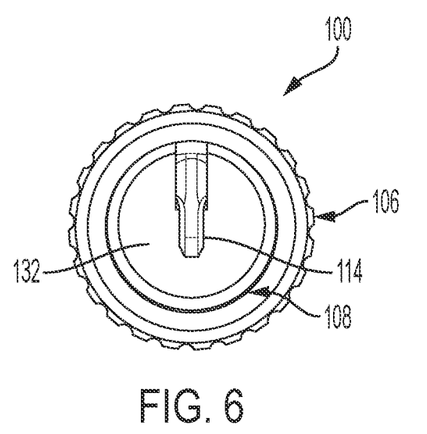
FIG. 6 is a distal end view of the intramedullary nail extractor of FIG. 1.
Figure 7:
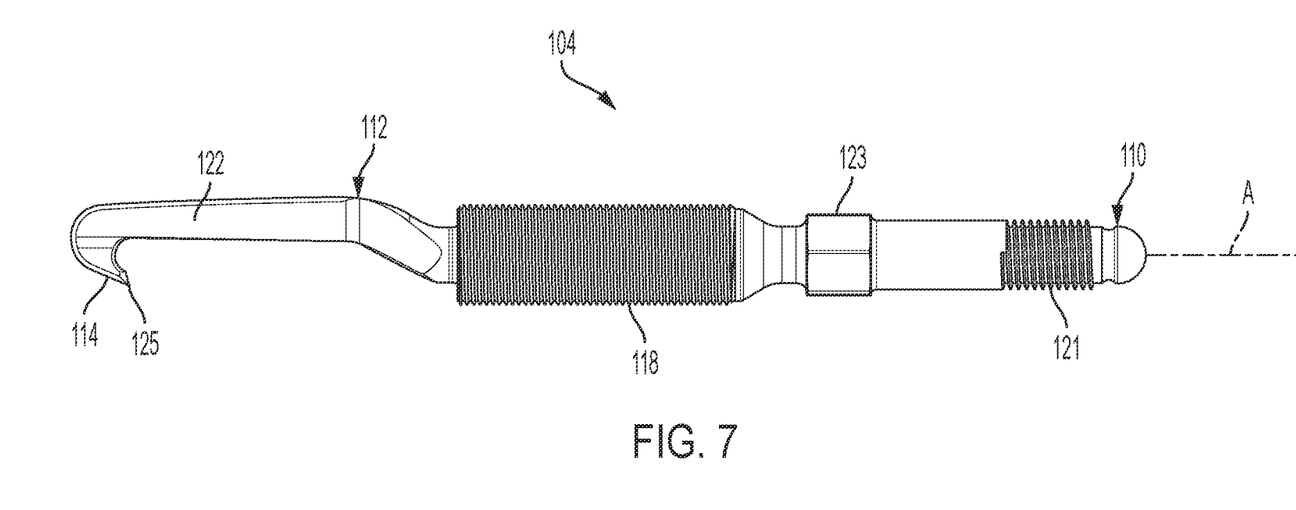
FIG. 7 is a side view of a central body of the intramedullary nail extractor of FIG. 1.

As best shown in FIG. 7, the distal end 112 of the central body 104 includes an arm 122 having a central longitudinal axis or longitudinal extent that can be radially offset from a longitudinal axis "A" of the central body. According to an aspect, the arm 122 can be offset from about 0 to 1 inch, including 0.1, 0.2, 0.3, 0.4, 0.5, 0.6, 0.7, 0.8 and 0.9 inch, from the longitudinal axis A of the central body. The distal end of the arm 122 terminates at the hook 114, a tip 125 of which is turned in a proximally facing direction. As best shown in FIGS. 3 and 4, the arm 122 is narrower than the remainder of the central body 104 to enable its passage through a longitudinally extending slot 136 (FIGS. 3, 4, 9A and 9B) provided in the clamping member 108, as described below. According to an aspect, the arm 122 has oppositely facing flat sides 122a, 122b which are adapted to be closely received in the longitudinally extending slot 136. As described in greater detail below, the hook 114 forms a first clamping portion and the clamping member 108 forms a second clamping portion which together operate to firmly clamp an intramedullary nail 102 for extraction of the intramedullary nail from a bone in which it is embedded.

The threaded intermediate portion 118 is located generally centrally of the central body 104. According to an exemplary embodiment, the length of the threaded intermediate portion 118 corresponds substantially to the length of the arm 122 and the length of the portion of the clamping member 108 that projects distally from the rotatable sleeve 106. Constructed as such, and depending on the position of the rotatable sleeve along the threaded intermediate portion, the hook 114 is capable of engaging an aperture 116 in the intramedullary nail 102 located up to approximately the length of the arm 122 from the proximal end of the intramedullary nail, or an aperture 116 located at a distance from the proximal end of the intramedullary nail less than the length of the arm 122.

As best shown in FIGS. 5 and 8A-8D, the rotatable sleeve 106 is a unitary rotatable sleeve threadedly engaged at threading 120 with the threaded intermediate portion 118 of the central body 104. The rotatable sleeve is engaged with the clamping member 108 at a proximal end 128 thereof via an annular groove 140, as described below. The outer diameter of the rotatable sleeve 106 is sized such that the sleeve may be comfortably and firmly gripped by a user. Additionally, the exterior surface of the rotatable sleeve may be provided with grip-enhancing structure such as knurling or ridges, as illustrated.

The clamping member 108 is configured as best shown in FIGS. 1-6, and 9A-9D. In accordance with an exemplary embodiment, the clamping member 108 is a clamping rod or cylinder having an open proximal end and a substantially closed distal end. The proximal end of the clamping member is cylindrical in shape so as to be receivable in the rotatable sleeve 106. While the clamping member is shown as being cylindrical throughout its length, it is understood that the distal end may assume any shape including, without limitation, triangular, square, oval, or the like. The sidewalls of the clamping member include a plurality of holes 130 (FIGS. 1-5, 9A and 9B) to facilitate cleaning and sterilization of the clamping member. The clamping member includes a distally facing distal end 132 for contacting the intramedullary nail 102 (FIG. 1) when in use. The distally facing distal end can be a planar end or a nonplanar end. The clamping member also includes a longitudinally extending slot 136 for passage of the hook 114 and arm 122 therethrough. Referring to FIGS. 9A-9D, the clamping member includes the longitudinally extending slot 136 for passage of the distal end 112 of the arm 122 therethrough. In addition, the clamping member preferably has a length sufficient to accommodate the entire length of the arm and the hook such that the hook is not exposed when the intramedullary nail extractor is not in use.

Figure 9A:
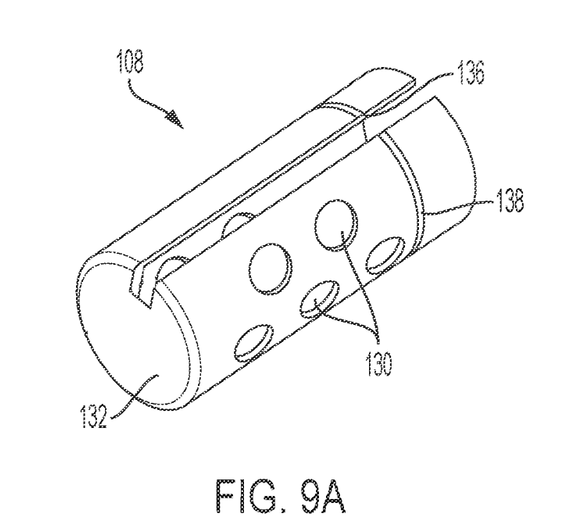
FIG. 9A is a distal end perspective view of a clamping member of the intramedullary nail extractor of FIG. 1.
Figure 9B:
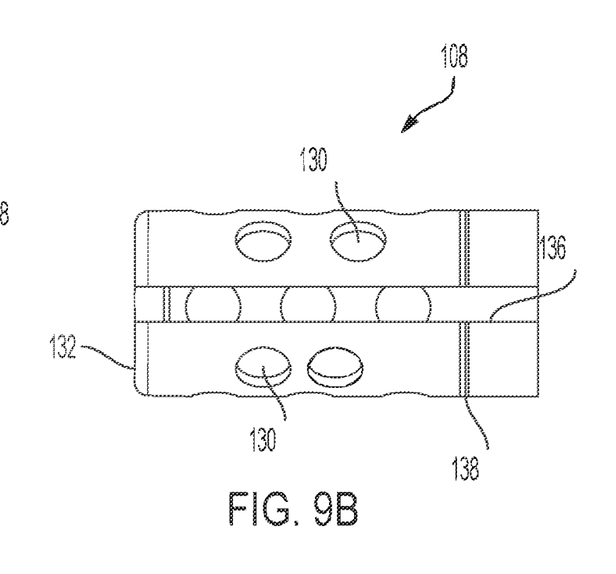
FIG. 9B is a side view of the clamping member of FIG. 9A.
Figure 9C:
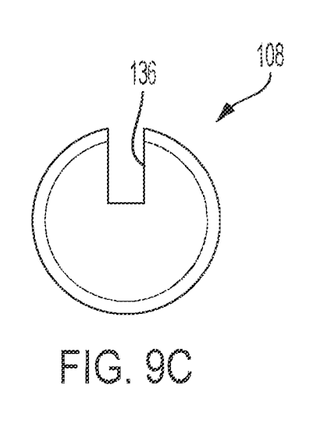
FIG. 9C is a proximal end view of the clamping member of FIG. 9A.
Figure 9D:
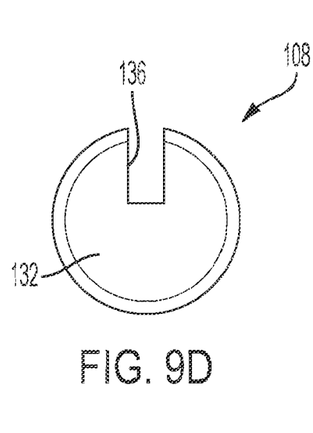
FIG. 9D is a distal end view of the clamping member of FIG. 9A.

As shown in FIGS. 9A and 9B, the clamping member also includes a raised annular ridge 138 configured for engaging, e.g., by snap-fit engagement, with the annular groove 140 provided in the rotatable sleeve 106 to allow rotation of the sleeve relative to the clamping member.

Figure 9E:
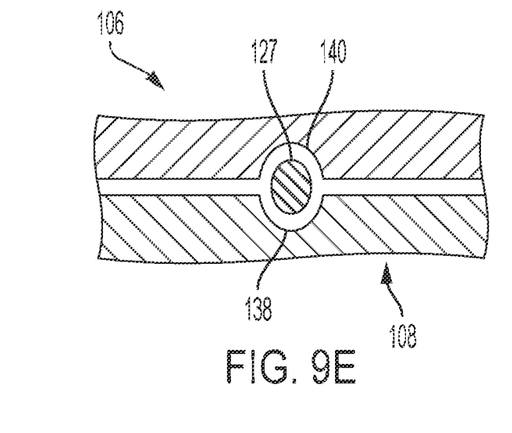
FIG. 9E is an enlarged cross-sectional view of an alternative arrangement for securing the clamping member to the rotatable sleeve.

Alternatively, the clamping member 108 can be retained within the rotatable sleeve 106 by a snap ring 127 (FIG. 9E) received in an annular groove 138' provided on the clamping member and in the annular groove 140 provided in the rotatable sleeve.

Figure 9F:
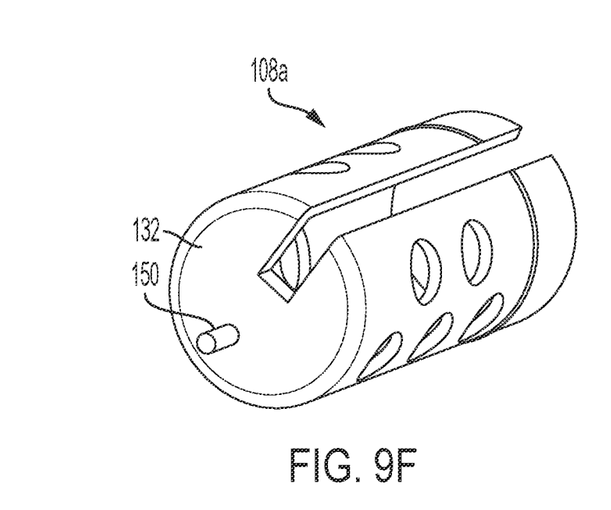
FIG. 9F is a distal end perspective view of another embodiment of a clamping member of the intramedullary nail extractor of FIG. 1.
Figure 9G:
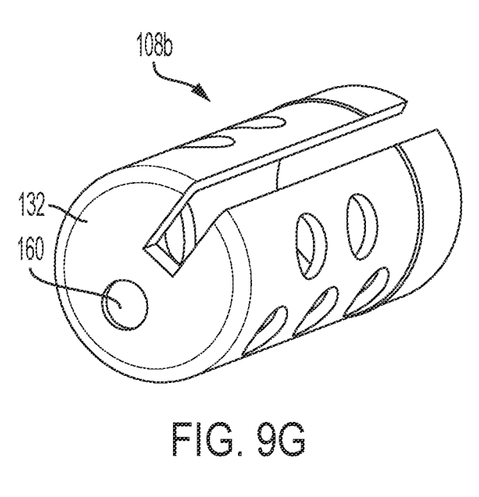
FIG. 9G is a distal end perspective view of another embodiment of a clamping member of the intramedullary nail extractor of FIG. 1.
Figure 9H:
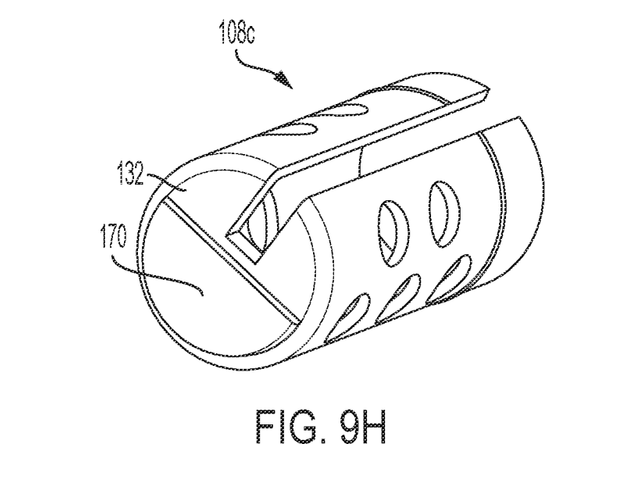
FIG. 9H is a distal end perspective view of another embodiment of a clamping member of the intramedullary nail extractor of FIG. 1.

FIGS. 9F, 9G and 9H illustrate alternative constructions of the clamping member identified respectively by reference numerals 108a, 108b and 108c which include various structures for preventing lateral movement of the cannulated nail when clamped between the clamping member and the hook 114. The clamping members 108a, 108b and 108c are constructed substantially similarly to clamping member 108. Accordingly, only those features of clamping members 108a, 108b and 108c that depart materially in structure and/or function from clamping member 108 will be described in detail.

Referring to FIG. 9F, the clamping member 108a is shown to include a pin 150 projecting distally from the distally facing distal end 132 of the clamping member. The pin 150 has a diameter sufficient to engage, i.e., be closely received in, the longitudinal opening 102a of the cannulated nail 102 in the manner shown in FIG. 1. The presence of the pin 150 in the cannulated nail serves to prevent lateral movement or slippage of the nail during an extraction procedure.

Referring to FIG. 9G, the clamping member 108b is shown to include a recess 160 in the form of a socket having a diameter sufficient to closely receive the outer circumference of a proximal end of the cannulated nail 102. The presence of the recess 160 in the distally facing distal end 132 of the clamping member serves to prevent lateral movement or slippage of the nail during an extraction procedure.

Referring to FIG. 9H, the clamping member 108c is shown to include a layer of high friction material 170 affixed to the distally facing distal end 132 of the clamping member for contacting the proximal end of the intramedullary nail 102. The high friction material may comprise an elastomer, e.g., silicone rubber, neoprene, or the like, or a polymer, e.g., a soft plastic, suitable for enhancing grip on the nail. The presence of the high friction material 170 on the distally facing distal end 132 of the clamping member serves to prevent lateral movement or slippage of the nail during an extraction procedure.

In operation, the user, e.g., a surgeon, rotates the rotatable sleeve 106 in a first direction causing the rotatable sleeves and the clamping member 108 to move in a proximal direction along the central body 104. Simultaneously, the hook 114 is caused to extend from the longitudinally extending slot 136 of the clamping member 108 until the tip 125 of the hook is capable of engaging the aperture 116 in the intramedullary nail 102. Once the hook is sufficiently extended and engages the aperture 116, the user turns the rotatable sleeve in the opposite direction, thereby causing the clamping member 108 to advance in a distal direction until the proximal end of the intramedullary nail is brought into firm contact with the distally facing end 132 of the clamping member 108. In such position, the hook 114 forms a first clamping portion and the clamping member 108 forms a second clamping portion which together operate to firmly clamp an intramedullary nail 102. It is understood that any of clamping members 108a, 108b or 108c may be substituted for clamping member 108 to further reduce the likelihood of lateral slippage of the intramedullary nail during extraction. In any event, with the intramedullary nail clamped by the hook to the clamping member, the user may exert a proximally directed force on the extractor 200 to extract the intramedullary nail from the bone in which it is embedded. Unlike conventional intramedullary nail extractors which tend to disengage from the intramedullary nail aperture 116 upon exertion of an extraction force, the intramedullary nail extractor according to the subject disclosure effectively clamps the intramedullary nail to assure that the intramedullary nail is reliably extracted upon the exertion of a sufficient extraction force.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as defined by the appended claims.

I claim:

1. An intramedullary nail extractor comprising:
  a central body that includes:
    a proximal end for attachment to an extractor, a distal end having a hook for engaging an intramedullary nail, and
a threaded intermediate portion between the proximal end and the distal end;
a rotatable sleeve threadedly engaging the threaded intermediate portion of the central body; and
a clamping member including a plurality of through holes and operatively engaged by the rotatable sleeve and moveable relative to the central body,
wherein the distal end of the central body is received in a longitudinally extending, radially open slot of the clamping member.

2. The intramedullary nail extractor of claim 1, wherein the clamping member is a clamping rod.

3. The intramedullary nail extractor of claim 1, wherein the clamping member includes a distally facing distal end for contacting the intramedullary nail.

4. The intramedullary nail extractor of claim 1, further comprising a raised annular ridge provided on the clamping member and configured for engaging an annular groove in the rotatable sleeve to retain the clamping member within the rotatable sleeve.

5. The intramedullary nail extractor of claim 1, wherein the hook includes an arm having a longitudinal axis that is radially offset from a longitudinal axis of the central body.

6. The intramedullary nail extractor of claim 1, wherein the clamping member includes a pin projecting distally from a distally facing distal end of the clamping member for engaging the intramedullary nail.

7. The intramedullary nail extractor of claim 1, wherein the clamping member includes a recess in a distally facing distal end of the clamping member for receiving the intramedullary nail.

8. The intramedullary nail extractor of claim 1, wherein the clamping member includes a high friction material affixed to a distally facing distal end of the clamping member for contacting the intramedullary nail.

9. An intramedullary nail extractor comprising:
a central body that includes:
    a proximal end for attachment to an extractor,
    a distal end having a first clamping portion for engaging an intramedullary nail, and
    a threaded intermediate portion between the proximal end and the distal end;
a rotatable sleeve threadedly engaging the threaded intermediate portion of the central body; and
a second clamping portion including a plurality of through holes and operatively engaged by the rotatable sleeve and moveable relative to the central body,
wherein the distal end of the central body is received in a longitudinally extending, radially open slot of the second clamping portion.

10. An intramedullary nail extractor comprising:
a central body that includes:
    a proximal end for attachment to an extractor,
    a distal end having a hook for engaging an intramedullary nail, wherein the hook includes an arm having oppositely facing flat sides and a longitudinal axis that is radially offset from a longitudinal axis of the central body, and
    a threaded intermediate portion between the proximal end and the distal end;
a rotatable sleeve threadedly engaging the threaded intermediate portion of the central body; and
a clamping member operatively engaged by the rotatable sleeve and moveable relative to the central body,
wherein the clamping member is a clamping rod and includes:
    a distally facing distal end for contacting the intramedullary nail,
    a plurality of through holes,
    a raised annular ridge configured for engaging an annular groove in the rotatable sleeve to retain the clamping member within the rotatable sleeve, and
    a longitudinally extending, radially open slot for passage of the distal end of the central body therethrough,
    wherein the oppositely facing flat sides of the arm are closely received in the longitudinally extending slot.

11. A method of extracting an intramedullary nail from bone comprising the steps of:
inserting the intramedullary nail extractor of claim 1 into the bone;
inserting the hook through an aperture of the intramedullary nail;
rotating the rotatable sleeve to secure the clamping member against the intramedullary nail; and
applying an extraction force to the proximal end of the central body.

* * * * *